United States Patent [19]

Green et al.

[11] Patent Number: 5,258,010
[45] Date of Patent: Nov. 2, 1993

[54] ANVILLESS SURGICAL APPARATUS FOR APPLYING SURGICAL FASTENERS

[75] Inventors: David T. Green, Westport; Henry Bolanos, East Norwalk; Henry R. Sienkiewicz, Stamford; Wayne C. Person, Newtown, all of Conn.

[73] Assignee: United States Surgical Corporation, Norwalk, Conn.

[21] Appl. No.: 982,025

[22] Filed: Nov. 24, 1992

Related U.S. Application Data

[63] Continuation of Ser. No. 707,683, May 30, 1991, abandoned.

[51] Int. Cl.$^5$ .............................................. A61B 17/00
[52] U.S. Cl. ................................. 606/219; 227/19; 227/176; 227/181
[58] Field of Search ............ 606/219; 227/19, 175–181

[56] References Cited

U.S. PATENT DOCUMENTS

| | | | |
|---|---|---|---|
| Re. 28,932 | 8/1976 | Noiles et al. | 227/19 |
| 3,275,212 | 9/1966 | Johnson . | |
| 3,643,851 | 2/1972 | Green et al. . | |
| 3,650,453 | 3/1972 | Smith, Jr. . | |
| 3,675,688 | 7/1972 | Bryan et al. . | |
| 3,819,100 | 6/1974 | Noiles et al. | 227/19 |
| 3,949,924 | 4/1976 | Green | 227/132 |
| 3,955,581 | 5/1976 | Spasiano et al. . | |
| 4,127,227 | 11/1978 | Green . | |
| 4,196,836 | 4/1980 | Becht . | |
| 4,204,623 | 5/1980 | Green | 227/19 |
| 4,403,693 | 9/1983 | Froehlich . | |
| 4,470,532 | 10/1984 | Froehlich . | |
| 4,478,362 | 10/1984 | Foslien . | |
| 4,505,273 | 3/1985 | Braun et al. . | |
| 4,523,695 | 6/1989 | Braun et al. | 227/19 |
| 4,527,726 | 7/1985 | Assell et al. | 227/19 |
| 4,583,670 | 4/1986 | Alvarado . | |
| 4,591,086 | 5/1986 | Campbell et al. . | |
| 4,592,498 | 6/1986 | Braun et al. | 227/19 |
| 4,596,350 | 6/1986 | Smith et al. . | |
| 4,618,086 | 10/1986 | Li et al. . | |
| 4,619,391 | 10/1986 | Sharkany et al. . | |
| 4,662,555 | 5/1987 | Thornton . | |
| 4,691,853 | 9/1987 | Storace . | |
| 4,796,793 | 1/1989 | Smith et al. . | |
| 4,807,628 | 2/1989 | Peters et al. . | |
| 4,813,586 | 3/1989 | Seifert . | |
| 4,887,756 | 12/1989 | Puchy . | |
| 4,951,860 | 8/1990 | Peters et al. . | |
| 4,976,686 | 12/1990 | Ball et al. | 604/61 |

*Primary Examiner*—Stephen C. Pellegrino
*Assistant Examiner*—Gary Jackson

[57] ABSTRACT

An anvilless surgical apparatus is provided for applying surgical fasteners to secure grafting material to a desired layer of tissue. The apparatus includes a housing having a nose portion at a distal end and a handle at its proximal end. A surgical fastener cartridge is mounted in the nose portion and is adapted to receive a plurality of surgical fasteners in longitudinal alignment therein. The cartridge is generally oriented substantially perpendicular to the handle. A drive shaft is provided within the housing for driving the surgical fasteners through the grafting material and at least partially into the layer of underlying tissue. The drive shaft is actuable by the handle and general has a pusher rod movable between a distal fired position and a retracted proximal loaded position. A releasing mechanism is provided in the handle for releasing the pusher rod from its retracted proximal position to cause it to thrust forward with sufficient force to contact a crown portion of a surgical fastener to drive it directly through the grafting material and at least partially into the tissue without forming a surgical fastener.

21 Claims, 7 Drawing Sheets

ANVILLESS SURGICAL APPARATUS FOR APPLYING SURGICAL FASTENERS

This is a continuation of division of copending application Ser. No. 07/707,683, filed on May 30, 1991, now abandoned.

FIELD OF THE INVENTION

This invention relates to surgical fasteners used in skin grafting and joining of body tissue and, more particularly, to apparatus for applying surgical fasteners composed of a material and configured to work their way out of body tissue after a limited period of time.

DESCRIPTION OF RELATED ART

Surgical fasteners have been used in operating procedures to eliminate the need for suturing, which is both time consuming and inconvenient. In many applications, the surgeon can use a stapler apparatus, i.e., a fastener implanting device loaded with one or more surgical fasteners, to accomplish in a few seconds what would have taken many minutes to perform by suturing. This reduction in operating time reduces blood loss and trauma to the patient.

A particularly useful procedure for use with surgical fasteners lies in the area of skin grafting. Currently, a wide variety of practitioners, including general surgeons, plastic surgeons, pediatricians and intensive care specialists perform a large percentage of the skin graft procedures done today. Some skin grafts are known as split-thickness grafts since they leave some dermis and are harvested from the patient using a dermatome. This device provides a uniform sheet of skin suitable for grafting. In many cases, the sheet graft is processed through a "meshing" or graft expanding device which makes the graft larger. This is particularly useful in patients experiencing bad burns and who have little healthy skin left after their injury. Meshing can typically expand the surface area of the graft up to three times its original dimensions.

The remaining types of grafts are full thickness grafts harvested using hand instruments and are typically used in plastic/reconstructive surgery, following trauma, cancer surgery, etc. In full thickness grafts, the entire dermis is removed.

It is preferred that the graft be smoothly and evenly applied to help prevent infection, necrosis, tenting, sloughing, and other complications. This requires that the graft match the underlying topography of the graft site to a high degree. Excessive tension in the graft will result in tenting or non-conformance which can cause graft failure.

In the past, surgical fasteners in the form of metal staples have been used to attach skin grafts. These metal staples are bent by the delivery apparatus to hook together body tissue. Such staples are typically made from biocompatible metals such as stainless steel alloys or titanium. Further, "splinting", in the form of synthetic grafts, fabric padding, or elastic bandages are also frequently used to insure wound cleanliness and to keep the graft in place. In some instances splinting is sometimes stapled in place over the original stapled graft.

The prior art includes many examples of surgical staplers which do not enclose the body tissue between an anvil and fastener holder. For example, surgical staplers such as those described in U.S. Pat. Nos. 3,643,851 and 4,618,086 approach the skin from one direction. However, these staplers require the use of staples which are malleable enough to be crimped by an anvil so that the prongs hook into the tissue. Typically, such staples are made of metal and are not bioabsorbable. They must be removed by another device such as a staple extractor which is not only time consuming but can cause discomfort and pain to the patient. The discomfort and pain in removal of the staples is especially acute when the fasteners are used in skin grafting a burn victim. The sensitivity of a burn patient's skin cannot be understated. Any contact with their skin causes distress let alone removal of fasteners inserted through the skin and embedded in underlying body tissue.

U.S. patent application Ser. No. 07/314,368, commonly assigned to United States Surgical Corporation, the contents of which are incorporated herein by reference, discloses a unique surgical fastener for securing skin grafts. The surgical fastener includes a crown portion and at least two projections which extend from the crown portion, preferably perpendicular to the crown portion and parallel to each other. Each projection includes a tapered tip portion to facilitate penetration into the body tissue and is configured to remain in the body for a relatively short period of time. The material of the projection also has a low coefficient of friction to facilitate ejection from the body tissue. This unique surgical fastener allows for the provision of lateral support across an incision or skin graft interface to provide sufficient lateral force between adjacent tissue sections.

Therefore, it is highly desirable to have an anvilless surgical apparatus for applying surgical fasteners to secure a graft to a layer of skin without causing excess discomfort to the patient.

SUMMARY OF THE INVENTION

According to the present invention, an anvilless surgical apparatus is provided for applying surgical fasteners to secure grafting material to a desired layer of tissue. The apparatus comprises a housing having a nose portion at a distal end and a handle at its proximal end. A surgical fastener cartridge is disposed in the nose portion and is adapted to receive a plurality of surgical fasteners in longitudinal alignment therein. The cartridge is generally oriented substantially perpendicular to the handle. Driving means is provided within the housing for driving the surgical fasteners through the grafting material and at least partially into the layer of underlying tissue. The driving means is actuable by the handle and generally comprises a pusher rod movable between a distal fired position and a retracted proximal prefired position. Releasing means are also provided in the handle for releasing the pusher rod from its retracted prefired position to cause it to thrust forward with sufficient force to contact a crown portion of a surgical fastener to drive it directly through the grafting material and at least partially into the underlying tissue without forming the projections of the surgical fastener.

A wide variety of surgical fasteners may be used with the present apparatus including both absorbable and non-absorbable type fasteners. Further, the surgical fastener cartridge may be removable and/or replaceable with a replacement cartridge. It is further envisioned that the nose portion may be rotatable so that the user may pre-set the angular orientation of the cartridge prior to firing.

BRIEF DESCRIPTION OF THE DRAWINGS

The accompanying drawings, referred to herein and constituting a part hereof, illustrate preferred embodiments of the present invention and, together with the description, serve to explain the principles of the present invention.

DETAILED DESCRIPTION OF THE PREFERRED EMBODIMENTS

Figure 1:
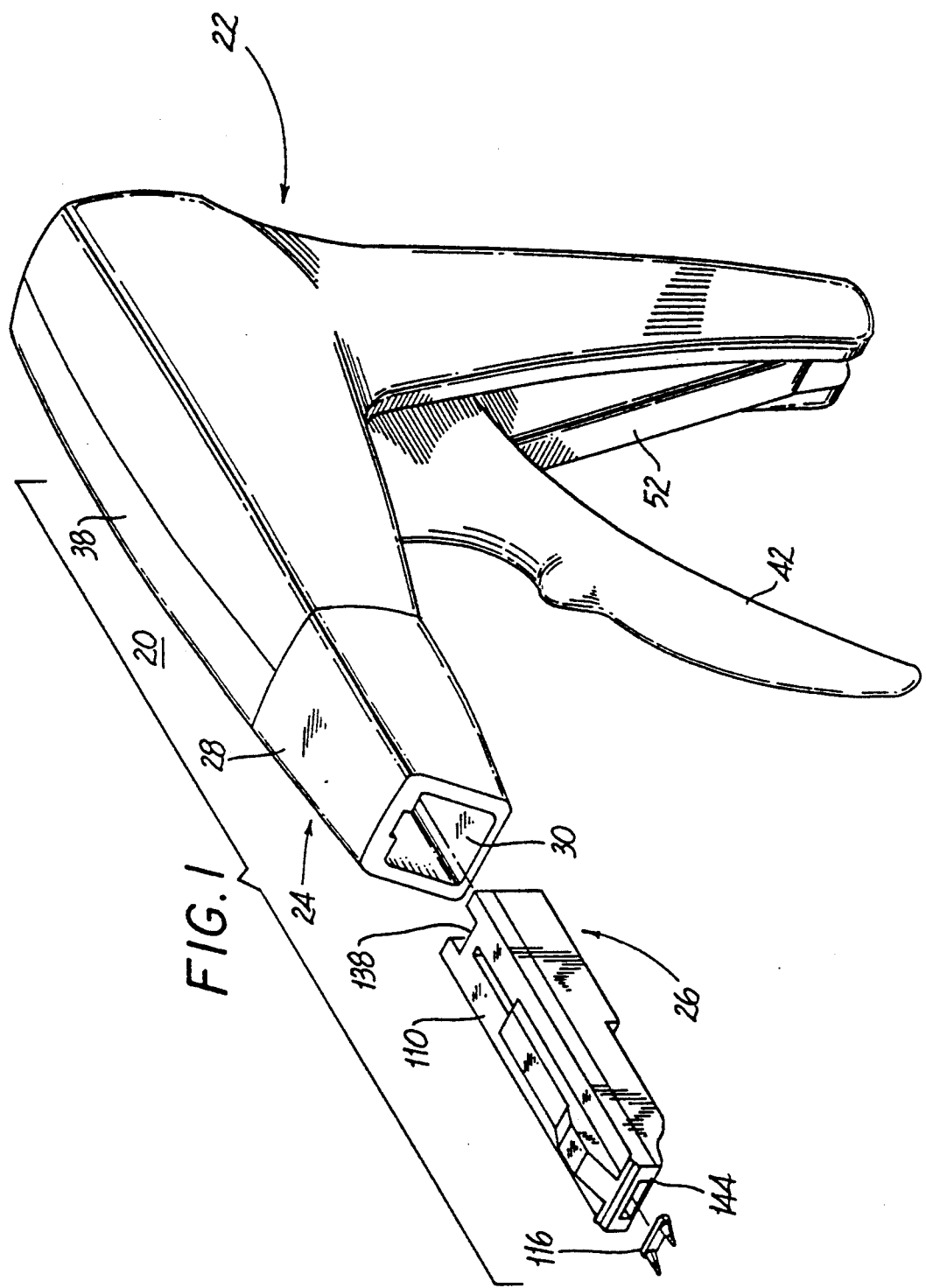
FIG. 1 is a perspective view of the present invention showing the handle, nose portion and removable surgical fastener cartridge.

Referring now to the drawings and, in particular, to FIG. 1, there is shown a preferred embodiment of the present anvilless surgical apparatus, shown generally at 20. The apparatus comprises a handle portion 22, a nose portion 24 and a cartridge portion 26. In the preferred embodiment shown in FIG. 1, the nose portion 24 is rotatably mounted to handle portion 22 and is further adapted to receive, in its distal end, an interchangeable cartridge portion 26. One of ordinary skill in the art will readily appreciate that where rotation is not desired nose portion 24 may be integrally formed with handle portion 22. Similarly, where reuse of the handle is not desired, the cartridge portion 26 may be integrally formed and the entire apparatus may be formed as a single use disposable unit.

Figure 2:
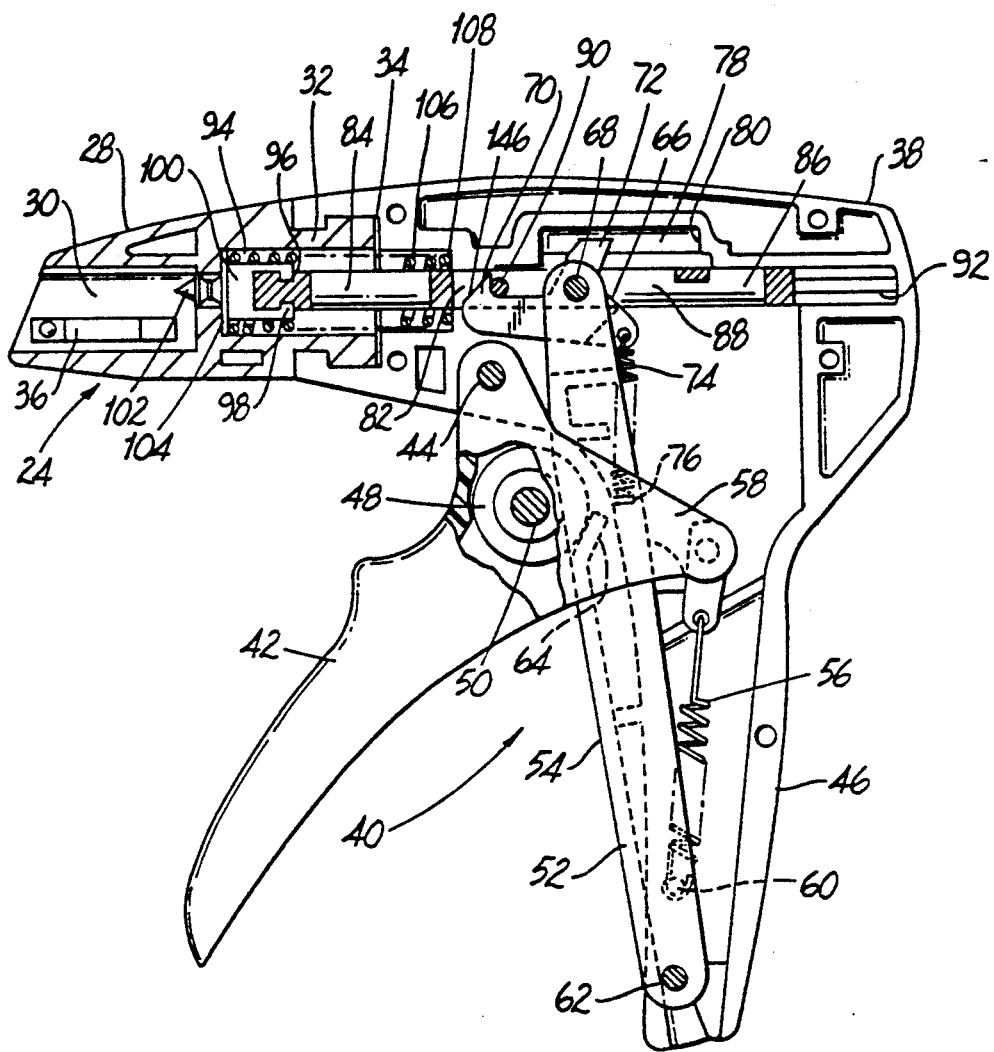
FIG. 2 is a side view in partial cross section of the handle and nose portion of the present invention.

FIG. 2 shows a cross-sectional view of the handle and nose portions 22, 24 of the anvilless surgical apparatus 20 of FIG. 1.

Nose portion 24 includes a housing 28 having a cartridge receiving section 30 in a distal end thereof. The proximal end of housing 28 has a flanged cylindrical element 32 formed therein to interfit with annular groove 34 formed in the distal end of handle portion 22. This allows nose portion 24 to be independently rotatable relative to handle portion 22 and allows the user to select a customized angular orientation for the intended operation. Cartridge receiving section 30 is substantially rectangular in shape and is adapted to receive and retain at least a proximal end of cartridge portion 26. A cartridge retainer spring 36 is disposed within cartridge receiving section 30 and serves to releasably engage cartridge portion 26 when it is in place within the cartridge receiving section 30.

Handle portion 22 includes a housing 38 within which is mounted a firing means shown generally at 40. The firing means 40 has a trigger 42 pivotally mounted in the housing 38 about pivot pin 44. Trigger 42 is adapted for movement between an extended prefired position with trigger 42 distal from hand grip 46 and a compressed fired position with trigger 42 proximal to hand grip 46. This operation will be discussed in greater detail below with respect to FIGS. 6-8. Roller 48 is disposed in trigger 42 and is rotatable therein about pin 50. Roller 48 engages pivot arm 52 and acts against the distal vertical surface 54 thereof as trigger 42 is retracted and released. A trigger return spring 56 is attached at a proximal projection 58 of trigger 42 and extends to fixed pin 60 formed in the hand grip 46 of housing 38. The trigger return spring 56 is in tension and serves to return trigger 42 to its extended distal most position.

Pivot arm 52 extends substantially vertically within hand grip 46 of housing 38 and is pivotal about pin 62. In the present embodiment an angular ramp 64 is formed in distal vertical surface 54 and serves as an action position for roller 48. This ramp 64 is configured to assist the initial pivotal movement of pivot arm 52 by trigger 42. A latch 66 is pivotally mounted in the uppermost portion of pivot arm 52 about pin 68. Latch 66 includes a hook shaped locking member 70 and a vertically oriented tab 72. A latch return spring 74 is connected in tension between latch 66 and fixed pin 76 and serves to maintain a clockwise pull on latch 66 relative to pin 68. A transverse cavity 78 is formed in housing 38 and serves to enclose tab 72 as pivot arm 52 reciprocates about pin 62. As tab 72 engages proximal vertical wall 80 of transverse cavity 78, latch 66 is driven to counterclockwise rotation about pin 68.

A drive shaft 82 extends longitudinally for reciprocal movement within housing 38 and includes a distal end 84, a proximal end 86 and a middle portion 88 therebetween. The middle portion of drive shaft 82 includes a transversely projecting pin 90 which engages hook shaped locking member 70 of latch 66. The proximal end 86 of drive shaft 82 moves longitudinally in channel 92 formed in housing 38. The channel 92 serves to guide drive shaft 82 in its reciprocal longitudinal motion.

The distal end 84 of drive shaft 82 is disposed within chamber 94 formed in housing 38 of the handle portion 22 and housing 28 of the nose portion 24. An annular groove 96 is formed in the distal end 84 of drive shaft 82 and engages projections 98 of tip assembly 100 to securely retain tip assembly 100 onto shaft 82. The tip assembly 100 includes a frustroconical engagement member 102 and a shoulder portion 104. The frustroconical engagement member 102 is accessible through cartridge receiving section 30 as will be described in greater detail below.

A compression spring 106 is disposed in chamber 94 and surrounds the distal end 84 of drive shaft 82. The compression spring 106 is bounded on a distal end by shoulder portion 104 and on a proximal end by shaft spacer washer 108. As the drive shaft 84 moves proximally within housing 38, the proximal movement of shoulder portion 104 serves to compress spring 106 against shaft spacer washer 108 in chamber 94.

Figure 3:
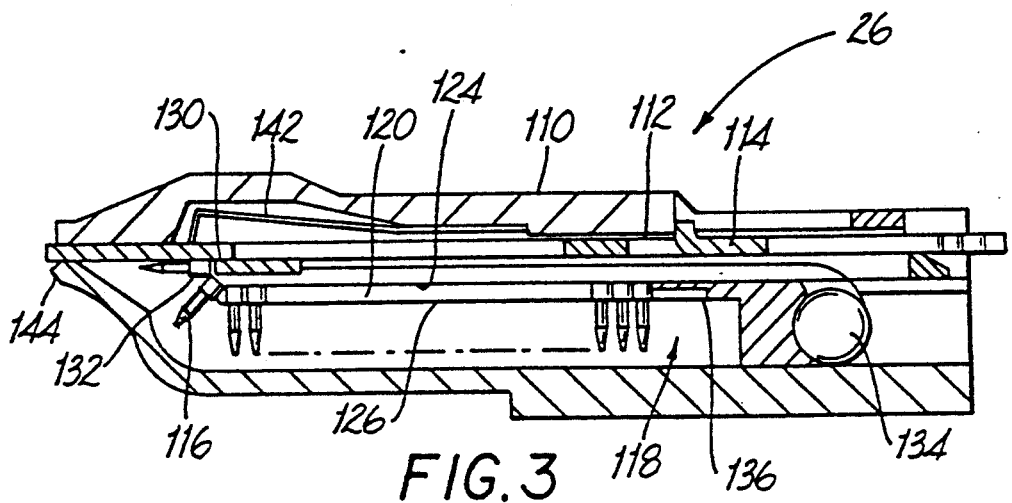
FIG. 3 is a side view in cross section of a fully loaded replaceable cartridge element in accordance with the present embodiment.
Figure 4:
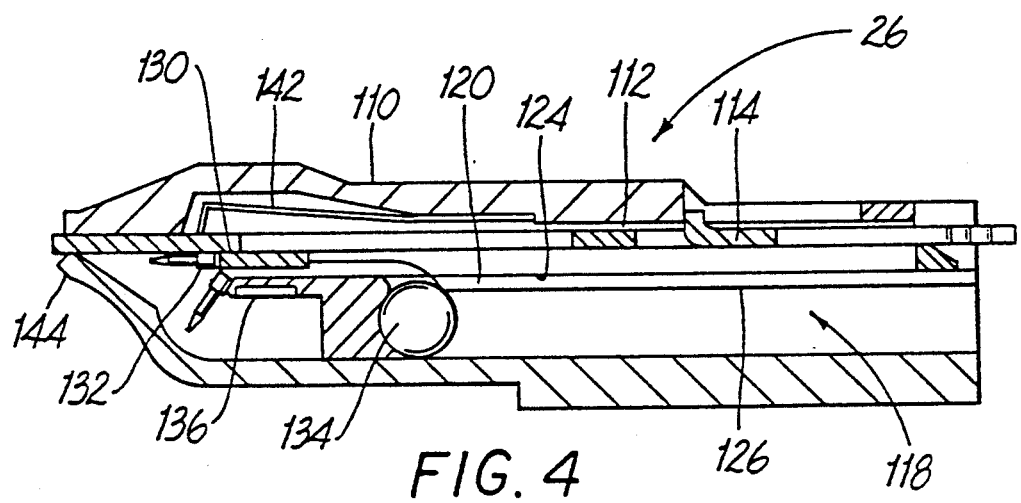
FIG. 4 is a side view in cross section of the replaceable cartridge element of FIG. 3 in a fully expended condition.

Referring now to FIGS. 3 and 4, there is shown a cartridge portion 26 in accordance with a preferred embodiment of the present invention. Cartridge portion 26 includes a housing 110 with a longitudinal channel 112 formed therein for receiving a driving member 114.

A plurality of surgical fasteners 116 (See FIG. 5) are disposed in a longitudinal magazine 118 positioned parallel to longitudinal channel 112. In the embodiment shown in FIGS. 3 and 4, magazine 118 is disposed beneath channel 112, however, one skilled in the art will readily appreciate that the magazine may be disposed above channel 112 if desired.

Magazine 118 includes a longitudinal channel 120 which supports and retains crown portion 122 of surgical fasteners 116 between a top wall 124 and a floor 126. Projections or prongs 128 of the surgical fasteners 116 are initially disposed vertically in the magazine 118. At a distal end of longitudinal channel 120, an angular ramp 130 formed in top wall 124 and floor 126 serves to guide surgical fasteners 116 into a distal vertical portion 132 effectively reorienting the surgical fasteners 116 such that projections 128 are horizontal and projecting distally of the cartridge portion 26. Constant force spring 134 serves to drive rigid follower 136 in abutment with the proximal most surgical fastener to sequentially move the respective distal most surgical fastener into longitudinal channel 112 in preparation for firing. Positioning spring 142 is disposed adjacent vertical portion 132 of channel 120 and serve to hold surgical fasteners 116 in place prior to firing.

Driving member 114 is adapted for reciprocal longitudinal motion within longitudinal channel 112. Locking projections 138 are formed in a proximal end of driving member 114 and, in this embodiment, serve to releasably engage with frustroconical engagement member 102 in a proximal end of cartridge receiving section 30. The distal end of driving member 114 has a substantially flat surface for a smooth interface between the driving member and the crown portion 122 of the surgical fastener 116 as it is fired out of opening 140 at the distal end of longitudinal channel 112. At least one spike 144 is positioned on the distal end of housing 110 in this embodiment to engage tissue and stabilize the apparatus in preparation for firing.

Figure 5:
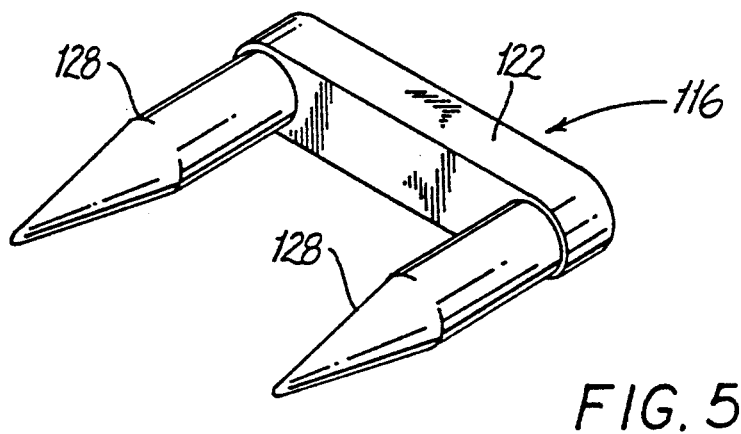
FIG. 5 is a perspective view of a surgical fastener for use with the present invention.

The anvilless surgical apparatus 20 shown and described herein is intended to apply surgical fasteners of the type shown in FIG. 5 and described in detail in corresponding U.S. patent application Ser. No. 07/314,368 commonly assigned herewith to United States Surgical Corporation, the contents of which are incorporated herein by reference. One skilled in the art, however, will readily appreciate that other surgical fastener designs may be used without departing from the inventive features of the present invention.

Figure 6:
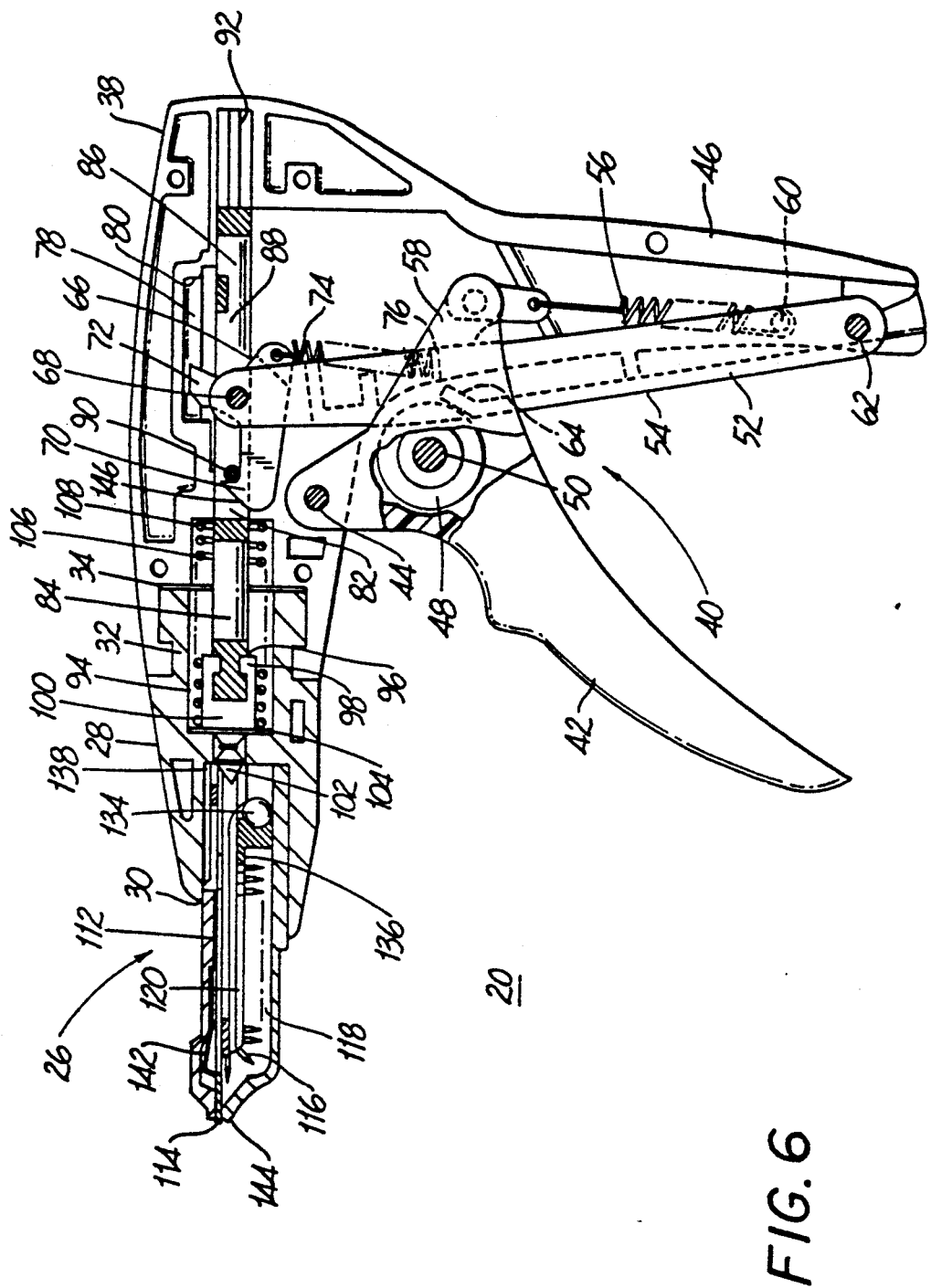
FIG. 6 is a side view in cross section of an anvilless surgical apparatus in the prefiring position.
Figure 7:
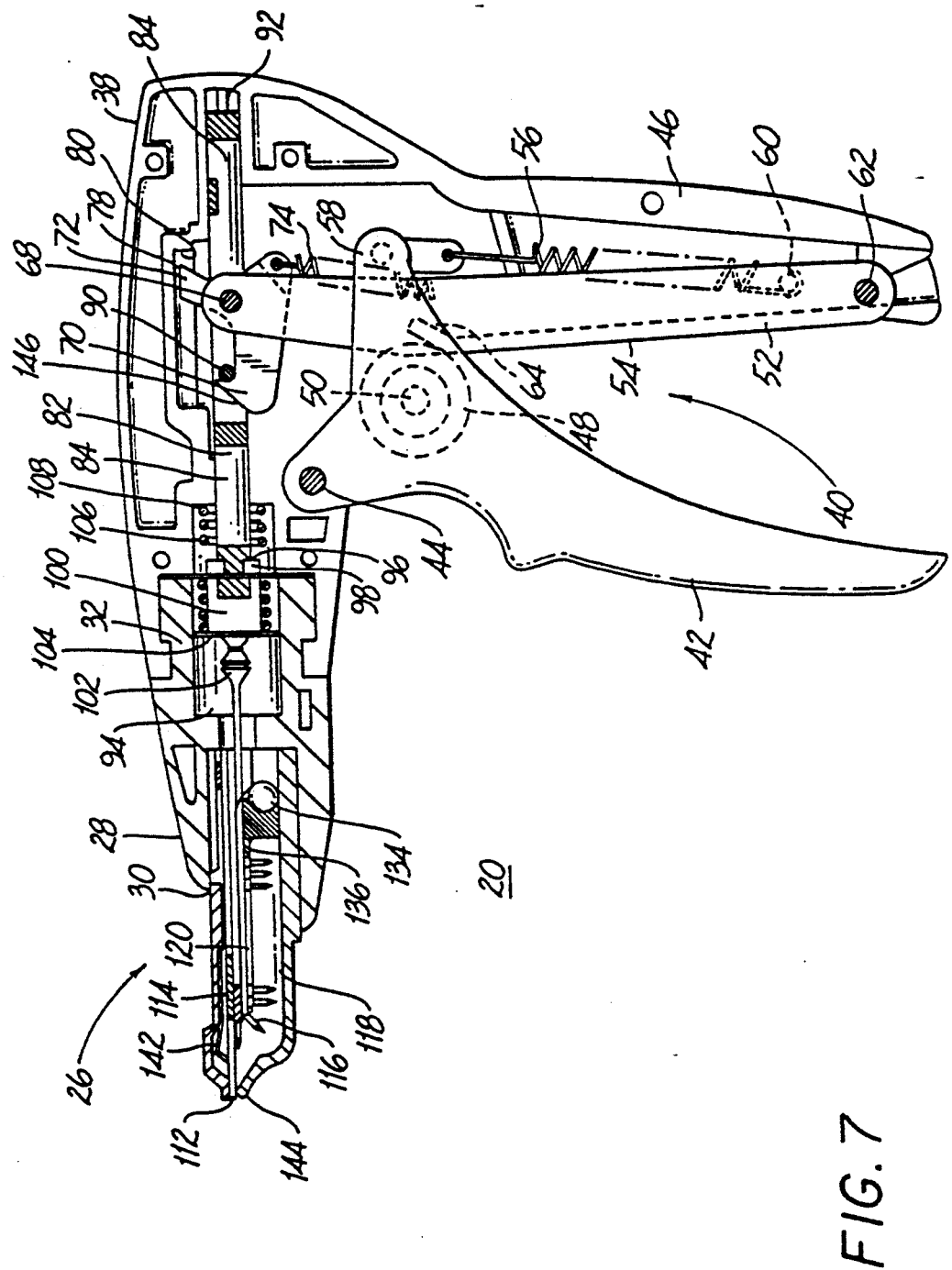
FIG. 7 is a side view in cross section of an anvilless surgical apparatus in a position just prior to firing.
Figure 8:
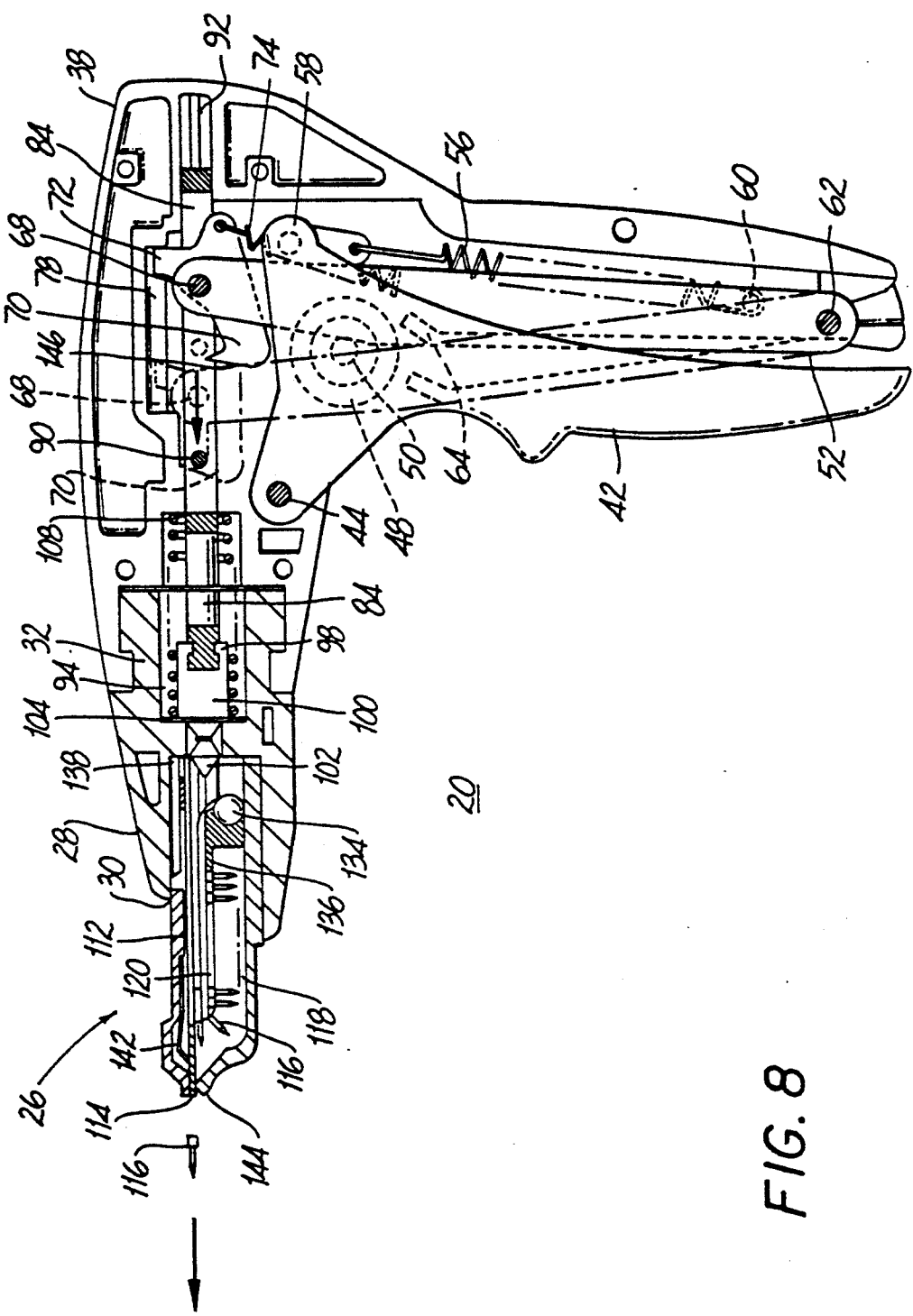
FIG. 8 is a side view in cross section of an anvilless surgical apparatus in the fired position.

Referring now to FIGS. 6–8, an anvilless surgical apparatus 20 in accordance with the present invention is shown in a sequence of operation. FIG. 6 shows the apparatus in the prefired position with the cartridge portion 26 in place within the cartridge receiving section 30 of nose portion 24. Locking projections 138 are engaged With frustroconical engagement member 102 such that both driving member 114 and drive shaft 82 move reciprocally longitudinally as a single unit in response to manipulation of the trigger 42. Hook shaped locking member 70 is engaged with transverse pin 90 and shaft 82 is in position to be retracted.

In FIG. 7, trigger 42 is moved proximally toward hand grip 46 causing roller 48 to move pivot arm 52 clockwise relative to pivot pin 62. This motion translates into proximal longitudinal motion of shaft 82 through latch 66 causing driving member 114 to retract in longitudinal channel 112. This motion compresses spring 106 and retracts drive member 114 allowing the distal most surgical fastener 116 in magazine 118 to be pushed into longitudinal channel 112 where it is held by positioning spring 142 in preparation for firing.

As the trigger 42 continues to move in a proximal direction toward hand grip 46, tab 72 of latch 66 approaches proximal vertical wall 80 of transverse cavity 78. Upon contacting wall 80, continued proximal motion of trigger 42 imparts a counterclockwise motion to latch 66 about pin 68 through tab 72. See FIG. 8. Hook shaped locking member 70 is pivoted out of engagement with pin 90 allowing the drive shaft 82/driving member 114 to be forcefully driven in a distal direction by the expansion of compression spring 106 against shoulder portion 104 of tip assembly 100. The distal end of driving member 114 contacts the crown portion 122 of surgical fastener 116 and drives it out of longitudinal channel 112 into tissue (not shown).

After firing has been completed, trigger return spring 56 and latch return spring 74 return the trigger 42 and latch 66 to their respective prefiring positions. As the latch 66 moves distally toward its original position, cam surface 146 on the distal end of hook-shaped locking member 70 abuts pin 90 and acts to reengage with the shaft 82 for subsequent refiring.

The present embodiment may be continuously refired in this manner until rigid follower 136 has reached the end of the horizontal portion of longitudinal channel 120 just prior to angular ramp 130. At this point, no further surgical fasteners 116 will be moved into horizontal channel 112 for driving. See FIG. 4. If continued applications are necessary, a new cartridge portion 26 may be substituted for the expended cartridge portion.

Figure 9:
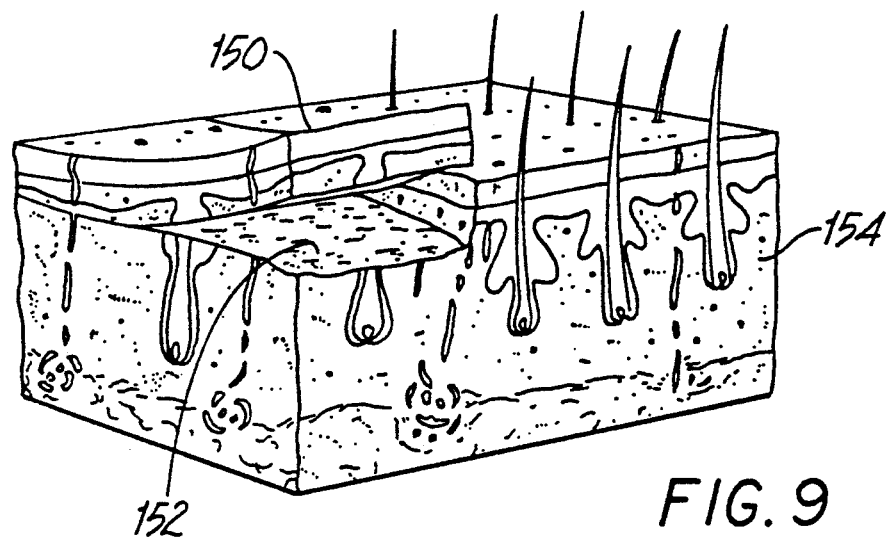
FIG. 9 is a perspective view in partial cross section of a graft being positioned on tissue.
Figure 10:
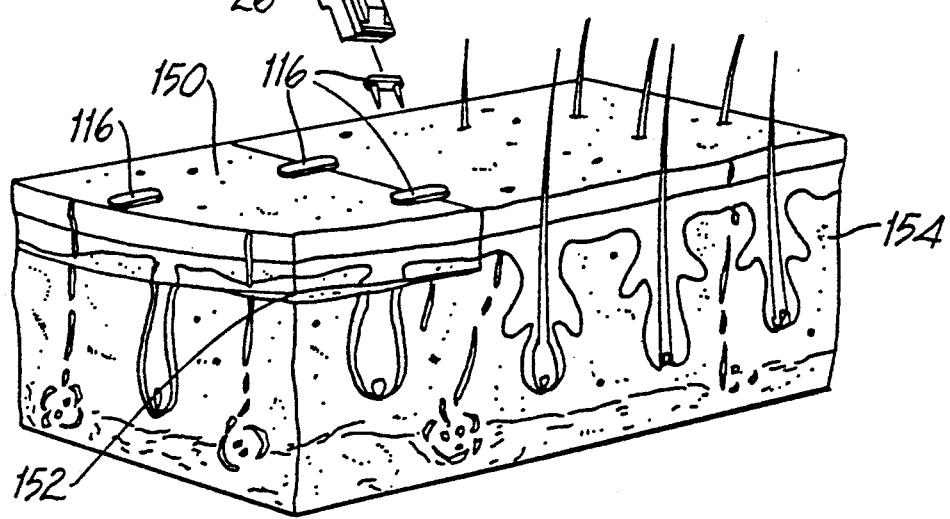
FIG. 10 is a perspective view in partial cross section of a graft being attached to tissue with an embodiment of the present invention.

FIGS. 9 and 10 show a split thickness skin graft 150 being applied and fastened into place on surrounding tissue 154. In FIG. 9 the graft 150 is trimmed to cover the damaged skin area 152. Thereafter, the graft is placed over the damaged area 152 and fastened into place using surgical fasteners 116 fired by the anvilless surgical apparatus 20 when the distal end of the magazine of the apparatus is placed in contact with the exposed surface of the graft (preferably at a 90° angle). These fasteners 116 may be applied around the periphery of the graft 150 to secure it adjacent healthy skin and, where desired, may be placed through the graft 150 and into underlying tissue 154.

To the extent not already indicated, it also will be understood by those of ordinary skill in the art that any one of the various specific embodiments herein described and illustrated may be further modified to incorporate features shown in other of the specific embodiments.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. An anvilless surgical apparatus for applying surgical fasteners to secure grafting material to tissue comprising:
   a housing having a nose portion at a distal end and a handle portion at a proximal end, said nose portion having a longitudinal axis;
   a surgical fastener cartridge mounted along said longitudinal axis of said nose portion substantially perpendicular to said handle portion, said cartridge having a plurality of surgical fasteners disposed therein which move along a path at least a portion of which is substantially parallel to said nose portion;

means for sequentially firing said surgical fasteners through said graft material and tissue, said means for driving being actuable by said handle and comprising a drive shaft movable between a distal fired position and a proximal prefired position; and means for releasing said drive shaft from said proximal prefired position to cause it to thrust forward to contact a crown portion of a surgical fastener to drive it directly into said graft material and tissue without forming the surgical fastener.

2. An anvilless surgical apparatus as in claim 1 wherein said nose portion is longitudinally rotatable relative to said handle portion.

3. An anvilless surgical apparatus as in claim 1 wherein said surgical fastener cartridge is a replaceable surgical fastener cartridge and is releasably mounted in said nose portion and replaceable with a new surgical fastener cartridge.

4. An anvilless surgical apparatus as in claim 3 wherein said drive shaft is divided into a driving member at leas partially disposed within said replaceable cartridge and replaceable therewith and a drive shaft disposed within said nose and handle portions.

5. An anvilless surgical apparatus as in claim 1 wherein said surgical fasteners are formed of a polymeric material.

6. An anvilless surgical apparatus as in claim 1 wherein said surgical fasteners are formed of a bioabsorbable material.

7. An anvilless surgical apparatus for applying surgical fasteners to secure grafting material to tissue comprising:

a housing having a handle portion at a proximal end and an independently rotatable nose portion at a distal end thereof, said nose portion having a longitudinal axis and further having a cartridge receiving section formed therein;

a replaceable surgical fastener cartridge releasably mounted along said longitudinal axis in said cartridge receiving section of said nose portion substantially perpendicular to said handle, said cartridge having a plurality of surgical fasteners disposed therein which move along a path at least a portion of which is substantially parallel with said nose portion;

firing means, at least partially disposed in said handle portion of said housing, having a longitudinally reciprocable spring loaded drive shaft movable between a distal fired position and a proximal prefired position; and actuating means including a trigger and means for retracting and releasing said drive shaft, said trigger interacting with said retracting and releasing means to move said drive shaft from a distal prefired position to a release position to cause it to thrust forward to contact a crown portion of a surgical fastener to drive it directly into graft material and tissue without forming the surgical fastener.

8. An anvilless surgical apparatus as in claim 7 wherein said surgical fasteners are formed of a polymeric material.

9. An anvilless surgical apparatus as in claim 7 wherein said surgical fasteners are formed of a bioabsorbable material.

10. An anvilless surgical apparatus as in claim 7 wherein said firing means includes a driving member at least partially disposed in said surgical fastener cartridge, said driving member being releasably attached to a distal end of said spring loaded drive shaft.

11. An anvilless surgical apparatus as in claim 7 wherein said means for retracting and releasing said drive shaft includes a spring loaded pivotal latching mechanism engageable with said drive shaft and being driven in longitudinal proximal motion by said trigger.

12. An anvilless surgical apparatus as in claim 7, said replaceable surgical fastener cartridge further comprising a rigid follower disposed in abutting relation to a proximal most surgical fastener in a longitudinal channel positioned parallel to a longitudinal plane formed by said drive shaft.

13. An anvilless surgical apparatus as in claim 12, said surgical fasteners disposed in said longitudinal channel having a crown portion and two extending projections, said surgical fasteners being disposed in said channel such that at least said crown portions are in abutting relation with said projections being oriented perpendicular to the longitudinal plane formed by said drive shaft, said longitudinal channel further comprising an angular ramp interconnecting a vertical section with said longitudinal channel so as to sequentially reorient said projections of said surgical fasteners in a longitudinal orientation in preparation for firing.

14. An anvilless surgical apparatus as in claim 12 further comprising at least one longitudinally oriented spike disposed in a distal face of said surgical fastener cartridge.

15. An anvilless surgical apparatus as in claim 13 further comprising a positioning spring disposed in said cartridge adjacent the distalmost surgical fastener and adapted to hold said surgical fastener in position for firing.

16. An anvilless surgical apparatus as in claim 7 wherein said cartridge receiving section formed in said nose portion further includes a cartridge retainer spring oriented to releasably engage said replaceable surgical fastener cartridge.

17. An anvilless surgical apparatus as in claim 7 wherein said grafting material comprises a synthetic mesh.

18. A method for securing a skin graft to an adjacent layer of skin comprising the steps of:

providing an anvilless surgical apparatus having a housing with a nose portion at a distal end and a handle portion at a proximal end, a surgical fastener cartridge longitudinally mounted in said nose portion substantially perpendicular to said handle portion said cartridge having a plurality of surgical fasteners disposed therein, means for sequentially firing said surgical fasteners into the graft material and the adjacent layer of skin, said means for driving being actuable by said handle and comprising a drive shaft movable between a distal fired position and a proximal prefired position, and means for releasing said drive shaft from said proximal prefired position to cause it to thrust forward to contact a crown portion of a surgical fastener to drive it directly into said graft material and adjacent layer of skin without forming the surgical fastener;

placing said nose portion of the apparatus atop a seam formed between said graft and said layer of skin; and firing a plurality of surgical fasteners through said graft and said layer of skin.

19. A method as in claim 18 wherein said surgical fasteners are bioabsorbable.

20. A method as in claim 18 further comprising the step of placing a bandage over the applied fastener to exert a vertical force to the fastener and to allow removal of some of the fasteners from said graft upon removal of said bandage.

21. A method as in claim 18 wherein each said fastener has a pair of prongs and the step of firing said fasteners causes one prong to engage the graft and the other prong to engage the adjacent layer of skin.

* * * * *